United States Patent [19]

Lindqvist

[11] Patent Number: 5,106,605

[45] Date of Patent: Apr. 21, 1992

[54] COLOR RESTORED RADIATION DISCOLORED SALT COMPOSITONS AND METHODS FOR COLOR RESTORATION

[75] Inventor: Sten-Börje Lindqvist, Veberöd, Sweden

[73] Assignee: Gambro AB, Sweden

[21] Appl. No.: 599,297

[22] Filed: Oct. 17, 1990

[30] Foreign Application Priority Data

Oct. 24, 1989 [SE] Sweden ................... 8903513

[51] Int. Cl.$^5$ ............................. C01B 31/24
[52] U.S. Cl. .................... 423/422; 204/901; 423/264; 423/499
[58] Field of Search ........... 423/264, 422, 499; 204/901

[56] References Cited

U.S. PATENT DOCUMENTS

| 2,817,579 | 12/1957 | Dropou ................... 423/264 |
| 3,414,422 | 12/1968 | Iannielli et al. ........... 423/264 |
| 3,518,064 | 6/1970 | Lenin ..................... 423/422 |
| 4,756,838 | 7/1988 | Veltman ................... 424/679 |
| 4,839,009 | 6/1989 | Pollack et al. ............ 204/157.48 |

Primary Examiner—Wayne Langel
Assistant Examiner—Stuart L. Hendrickson
Attorney, Agent, or Firm—Lerner, David, Littenberg, Krumholz & Mentlik

[57] ABSTRACT

Salt compositions which have been discolored during sterilization by means of radioactive radiation such as gamma and/or beta irradiation of the type which causes such discoloration are substantially restored to the original color by treatments disclosed herein. Methods for restoring the original color of such salts, including heating to specified temperatures for specified periods of treatment are also disclosed.

9 Claims, No Drawings

COLOR RESTORED RADIATION DISCOLORED SALT COMPOSITONS AND METHODS FOR COLOR RESTORATION

FIELD OF THE INVENTION

The present invention relates to salt compositions which have become discolored by sterilization by radioactive radiation, e.g., gamma irradiation and/or beta irradiation. More particularly, the present invention relates to salts which are intended to be used for medical purposes, e.g., in dialysis, for the preparation of dialysis liquids.

BACKGROUND OF THE INVENTION

It is known that salts which have been sterilized by radioactive radiation become discolored. A probable explanation of this discoloration is that it is due to an electron displacement, that is to say to one or more electrons being caused to change their electron orbit, and thereby entering into an excited state.

Unpublished experiments which have been directed to restoring the original color of these irradiated salts have been carried out with the help of daylight, UV-light and microwaves. However, these experiments have not evidenced any success.

Alternatively, it is possible to refrain entirely from the use of such irradiation, and to use instead a bacteria filter for the filtering out of undesirable substances after the salt has been dissolved in water or other suitable liquids In this case, however, difficulties can arise in maintaining the bacteria filter sterile. These difficulties may be overcome in the manner which is described, for example, in U.S. Pat. No. 4,783,273.

A further alternative method to such irradiation consists in using a powder which is as pure as possible, and dissolving that powder directly in connection with its utilization, see, for example, U.S. Pat. No. 4,784,495. It is not possible in such case, however, to guarantee absolute sterility.

SUMMARY OF THE INVENTION

In accordance with the present invention, salt compositions having an original color and which have been sterilized by means of radioactive radiation are rendered substantially free of discoloration by treating the sterilized salts so as to substantially restore their original color thereto. Thus, such salts which have been sterilized by radioactive irradiation, such as gamma or beta irradiation of the type which causes such discoloration upon use, has its original color wholly or partly restored, preferably by the application of heat. The treating of the sterilized salt comprises applying sufficient heat to the sterilized salt for a sufficient period of time to restore its original color. In another embodiment, the treating comprises recrystallizing the sterilized salt in a sterile environment.

In accordance with a preferred embodiment of the salt compositions of the present invention, the salt compositions themselves are sodium hydrogen carbonate and/or sodium chloride, which are salts frequently used in connection with procedures such as dialysis, hemofiltration and plasmaphoresis. These salts may be dissolved directly in conjunction with these medical treatments as is described in aforementioned U.S. Pat. No. 4,784,495. By such use it is, however, also desirable for the powder to be present in the form of a wholly sterile naturally colored powder.

In accordance with the method of the present invention, the original color of a salt composition which has been discolored during sterilization by means of radioactive radiation is restored by a method comprising treating the discolored salt composition so as to substantially restore its original color. Preferably, the treating comprises applying sufficient heat to the sterilized salt for a sufficient period of time to restore its original color.

Insofar as the treatment of irradiated sodium hydrogen carbonate is concerned, the temperature and duration of treatment may be selected from the following approximate schedules:

a) one day at 65° C., resulting in a diminishing discoloration;
b) three days at 75° C., resulting in a natural-colored, substantially white powder;
c) one day at 85° C., resulting in a natural-colored, substantially white powder;
d) 6 hours at 95° C., resulting in a natural-colored, substantially white powder; and
e) 3 hours at 105° C., resulting in a natural-colored, substantially white powder.

It should be noted in this regard that one days' treatment at approximately 55° C. did not produce any objectively detectable change of color.

Furthermore, it has also been found that no changes of the effective temperatures or durations of treatment were required when changing the irradiation dose for sodium hydrogen carbonate from 25 kGy to 50 kGy. On the other hand, it has been established that sodium hydrogen carbonate of analytically pure quality obtains a coloration which has less of a pink color than that of the corresponding standard quality for medical usage. Furthermore, the sodium hydrogen carbonate which is preferably employed in medical treatments such as those described in U.S. Pat. No. 4,784,495 generally has a granular size of between about 130 and 500 $\mu$m. It has been found that these granules exhibit the color changes upon irradiation as discussed herein. However, particles on the order of under about 10 $\mu$m do not appear to exhibit such color change to the naked eye, probably due to the altered reflection and spread of light affected by these smaller crystals. However, particles of such a small size would not be useful in connection with medical treatments of the type disclosed in U.S. Pat. No. 4,784,495 due to the high flow resistance created thereby.

Insofar as the treatment of irradiated sodium chloride is concerned, the temperature and duration of treatment may be selected from the following approximate schedule: one day at 150° C., resulting in a natural-colored, substantially white powder.

It should be noted in this regard that one day's treatment at 100° C. proved to have no effect on the powder which had been colored orange-brown as a result of irradiation.

Alternatively, the discoloration can be eliminated by means of recrystallization with the use of sterile water. In this process, a saturated solution is produced from which the salt can be re-precipitated to thereafter be separated from the surplus liquid and dried. This entire procedure must, of course, be carried out in a completely sterile environment, and the same applies to subsequent storage which may be done, for example, in small, completely bacteria-tight packages.

This invention is not limited solely to the examples described above, but can be varied within the framework of the subsequent claims. For example, it will be clear to those versed in the art that there are probably common properties of many salts which bring about the discoloration obtained during radioactive irradiation. For this reason it should be possible for many salts other than those mentioned as examples to be treated by the method in accordance with the invention.

What is claimed is:

1. A method for restoring the original color of a sodium bicarbonate salt composition which has been discolored during sterilization by means of radioactive radiation comprising heating said discolored salt composition to a temperature greater than about 65° C. for a sufficient period of time so as to substantially restore said original color thereto.

2. The method of claim 1 wherein said treating comprises heating said salt composition for about one day at about 65° C.

3. The method of claim 1 wherein said treating comprises heating said salt composition for about three days at about 75° C.

4. The method of claim 1 wherein said treating comprises heating said salt composition for about one day at about 85° C.

5. The method of claim 1 wherein said treating comprises heating said salt composition for about six hours at about 95° C.

6. The method of claim 1 wherein said treating comprises heating said salt composition for about three hours at about 105° C.

7. The method of claim 1 wherein said radioactive radiation is applied at a dosage of between about 25 and 50 kGy.

8. A method for restoring the original color of a salt composition consisting essentially of sodium bicarbonate which has been discolored during sterilization by means of radioactive radiation comprising recrystallizing said discolored salt composition in a sterile environment so as to substantially restore said original color thereto.

9. The method of claim 8 wherein said treating comprises preparing a saturated solution of said discolored salt composition in sterile water, precipitating said saturated solution, separating said substantially restored salt composition, and drying said separated salt composition.

* * * * *